(12) United States Patent
Purich

(10) Patent No.: US 9,962,430 B2
(45) Date of Patent: May 8, 2018

(54) METHODS FOR TREATING PAIN ASSOCIATED WITH CHRONIC PANCREATITIS

(71) Applicant: CHIRHOCLIN, INC., Burtonsville, MD (US)

(72) Inventor: Edward D. Purich, Silver Spring, MD (US)

(73) Assignee: CHIRHOCLIN, INC., Burtonsville, MD (US)

( * ) Notice: Subject to any disclaimer, the term of this patent is extended or adjusted under 35 U.S.C. 154(b) by 0 days. days.

(21) Appl. No.: 14/374,147

(22) PCT Filed: Feb. 13, 2013

(86) PCT No.: PCT/US2013/025820
§ 371 (c)(1),
(2) Date: Jul. 23, 2014

(87) PCT Pub. No.: WO2013/122979
PCT Pub. Date: Aug. 22, 2013

(65) Prior Publication Data
US 2014/0349939 A1 Nov. 27, 2014

Related U.S. Application Data

(60) Provisional application No. 61/598,948, filed on Feb. 15, 2012.

(51) Int. Cl.
*A61K 38/22* (2006.01)
(52) U.S. Cl.
CPC .................................. *A61K 38/2235* (2013.01)
(58) Field of Classification Search
CPC .................................................. A61K 38/2235
See application file for complete search history.

(56) References Cited

U.S. PATENT DOCUMENTS

| | | | |
|---|---|---|---|
| 4,246,374 A | 1/1981 | Kopchik | |
| 4,278,751 A | 7/1981 | Specht et al. | |
| 4,366,228 A | 12/1982 | Specht et al. | |
| 4,491,628 A | 1/1985 | Ito et al. | |
| 4,548,891 A | 10/1985 | Riediker et al. | |
| 4,585,876 A | 4/1986 | Fischer et al. | |
| 4,681,959 A | 7/1987 | Ayen et al. | |
| 5,019,482 A | 5/1991 | Al et al. | |
| 5,049,628 A | 9/1991 | Nawata et al. | |
| 5,215,863 A | 6/1993 | Nawata et al. | |
| 5,492,793 A | 2/1996 | Breyta et al. | |
| 5,538,821 A | 7/1996 | Kakinuma et al. | |
| 5,545,702 A | 8/1996 | Oishi et al. | |
| 6,042,997 A | 3/2000 | Barclay et al. | |
| 6,284,185 B1 | 9/2001 | Tokuda et al. | |
| 6,294,239 B1 | 9/2001 | Tokuda et al. | |
| 6,524,708 B2 | 2/2003 | Puligadda et al. | |
| 6,602,646 B1 | 8/2003 | Sato et al. | |
| 6,730,452 B2 | 5/2004 | Brock et al. | |
| 7,358,027 B2 | 4/2008 | Ito et al. | |
| 7,359,108 B2 | 4/2008 | Hayes et al. | |
| 7,381,698 B2 | 6/2008 | Fein et al. | |
| 7,459,155 B2 | 12/2008 | Margolin et al. | |
| 7,479,364 B2 | 1/2009 | Ito | |
| 7,800,816 B2 | 9/2010 | Hayes et al. | |
| 7,813,030 B2 | 9/2010 | Lo et al. | |
| 2005/0070472 A1 | 3/2005 | Gedulin et al. | |
| 2005/0129675 A1 | 6/2005 | Fein et al. | |
| 2006/0002912 A1 | 1/2006 | Fein et al. | |
| 2006/0019347 A1 | 1/2006 | Cho et al. | |
| 2007/0219222 A1 | 9/2007 | Moran et al. | |
| 2008/0146611 A1 | 6/2008 | Moran et al. | |
| 2009/0081184 A1 | 3/2009 | Margolin et al. | |
| 2009/0143377 A1 | 6/2009 | Ng et al. | |
| 2009/0192558 A1 | 7/2009 | Whitehurst et al. | |
| 2010/0048472 A1 | 2/2010 | Rosen et al. | |
| 2010/0197586 A1 | 8/2010 | Bevec et al. | |
| 2010/0204313 A1 | 8/2010 | Pasricha | |

FOREIGN PATENT DOCUMENTS

SU 624635 A * 8/1978 ............. A61K 37/24

OTHER PUBLICATIONS

Chey et al, Secretin Historical Perspective and Current Status, Pancreas, 2014, 43, pp. 162-182.*
Acute and Chronic Pancreatitis, from http://rezidentiat.3x.ro/eng/pancreatitaeng.htm, pp. 1-15, accessed Dec. 11, 2015.*
Acute and Chronic Pancreatitis, from http://web.archive.org/web/20091030012855/http://rezidentiat.3x.ro/eng/pancreatitaeng.htm, pp. 1-16, available online on Oct. 30, 2009.*
SecreFlo (Secretin), from http://www.rxlist.com/secreflo-drug/clinical-pharmacology.htm, pp. 1-3, accessed May 23, 2016.*
Machine translation of SU 624635 A, pp. 1-4, accessed May 24, 2016.*
Mass of an Adult, from https://hypertextbook.com/facts/2003/AlexSchlessingerman.shtml, pp. 1-4, accessed Aug. 6, 2017.*
Goulden, The pain of chronic pancreatitis: a persistent clinical challenge, British Journal of Pain, 2013, 7, pp. 8-22.*
International Preliminary Report on Patentability and Written Opinion of the International Searching Authority for International Patent Application No. PCT/US2013/025820; dated Aug. 19, 2014; 6 Pages.
International Search Report for International Patent Application No. PCT/US2013/025820; International Filing Date: Feb. 13, 2013; dated Apr. 23, 2013; 2 Pages.

(Continued)

*Primary Examiner* — Julie Ha
*Assistant Examiner* — Li N Komatsu
(74) *Attorney, Agent, or Firm* — Cantor Colburn LLP

(57) ABSTRACT

The invention relates generally to methods for treating pain associated with chronic pancreatitis in patients. The methods comprise administering a therapeutically effective amount of a pharmaceutical composition comprising secretin and a pharmaceutically acceptable carrier.

13 Claims, 1 Drawing Sheet

(56) References Cited

OTHER PUBLICATIONS

Tympner et al., "The Treatment of Chronic Recurrent Pancreatitis with Depot Secretin—a Preliminary Report" Hepato-gastroenterol, 33, (1986), pp. 159-162.
Guy et al.; "Protein Content of Precipitates Present in Pancreatic Juice of Alcoholic Subjects and Patients with Chronic Calcifying Pancreatitis"; Gastroenterology; vol. 84; Jan. 1983; pp. 102-107.
Kiem et al.; "Failure of Secretin to Prevent or Ameliorate Cerulein-induced Pancreatitis in the Rat"; Hepatogastroenterology; vol. 32; 1985; pp. 91-96.
Kuiper et al.; "Diagnostic Efficacy of the Secretin Stimulation Test for the Zollinger-Ellison Syndrome: An Intra-Individual Comparison Using Different Dosages in Patients and Controls"; Pancreatology; vol. 10; 2010; pp. 14-18.
Lankisch et al.; "Influence of Secretin on the Course of Acute Experimental Pancreatis in Rats"; Digestion; vol. 26; 1983; pp. 187-191.
Madsen et al.; "The intraductal Pancreatic Pressure in Chronic Obstructive Pancreatitis" ; Scand. J. Gastroenterol.; vol. 17; 1982; pp. 553-554.
Noda et al.; "Bromhexine Hydrochloride Eliminates Protein Plugs and Relieves Attacks of Pancreatitis"; Pancreas; col. 15, No. 2; 1997; pp. 209-2011.
Renner et al.; "Protective Effects of Exogenous Secretin on Ceruletide-induced Acute Pancreatitis in the Rat"; J. Clin. Invest.; vol. 72; Sep. 1983; pp. 1081-1092.
Shinohara et al.; "A case of mucin-producing bile duct tumor which responded to bromhexine hydrochloride treatment and radiotherapy"; Tando; vol. 7; 1993; pp. 527-534, Abstract only.
Tsujimoto et al.; "Effect of Bromhexine Hydrochloride Therapy for Alcholic Chronic Pancreatitis"; Alcohol. Clin. Exp. Res.; vol. 29, No. 12; Dec. 2005; pp. 272S-276S.
Tympner et al.; "Viscosity and Trypsin Activity of Pure Pancreatic Juice in Chronic Pancreatitis"; Acta Hepatogastroenterol.; vol. 25; 1978; pp. 73-76.
Yamamoto et al.; "Double Doses of Secretin Contribute to Diagnosis of Zollinger-Ellison Syndrome in Secretin adn Selective Arterial Secretion Injection Tests—A Case Report"; Digestive Dis. and Sci.; vol. 50 No. 11; Nov. 2005; pp. 2034-2036.

\* cited by examiner

METHODS FOR TREATING PAIN ASSOCIATED WITH CHRONIC PANCREATITIS

CROSS-REFERENCE TO RELATED APPLICATIONS

This Application is a U.S. National Stage Application of PCT/US2013/025820 filed Feb. 13, 2013 which claims priority to U.S. Provisional Patent Application No. 61/598,948 filed Feb. 15, 2012, both of which are incorporated by reference in their entirety.

BACKGROUND OF THE INVENTION

1. Field of the Invention

The invention relates generally to methods for treating pain associated with chronic pancreatitis in patients. The methods comprise administering a therapeutically effective amount of a pharmaceutical composition comprising human or porcine secretin and a pharmaceutically acceptable carrier.

2. Brief Description of the Related Art

Chronic pancreatitis (CP) is a long-standing inflammation of the pancreas that alters its normal structure and functions. Chronic pancreatitis can present as episodes of acute inflammation in a previously injured pancreas, or as chronic damage with persistent pain or malabsorption. Inflammation of the pancreas that is associated with chronic pancreatitis generally does not heal or improve, gets worse over time, and leads to permanent damage. The inflammation can cause the pancreas to reduce production of enzymes necessary for digestion of fats and other food components. The inflammation is associated with premature activation of trypsin a proteolytic enzyme normally secreted by the pancreas for digestion of food. Pancreatic fluid is produced by the pancreas upon stimulation of the hind brain by human secretin. Stimulation of the pancreas by secretin will wash any activated trypsin from the pancreas ducts and by this action reduce irritation and inflammation by trypsin residues that may have been left in the pancreatic ducts. The presence of mucous or thick pancreatic secretions has been associated with mutations in the CFTR gene and stimulation of pancreatic fluid flow may reduce the mucous in the pancreatic ducts. Human and porcine secretins are associated with Vasoactive Intestinal Peptide (VIP) receptors that are found throughout the brain. In addition, the avidity of human secretin to VIP receptors may be responsible for central pain reduction in conjunction with opioids.

Chronic pain is the primary symptom of chronic pancreatitis. Pain management has been a challenge in this disease, with multiple modalities attempted for use. Pancreatic rest using pancreatic enzyme supplementation, opioid analgesics, nerve blocks, and antioxidants are currently considered the mainstays in treatment that is not amenable to operative intervention. Unfortunately, even with all of these options, pain remains a prominent and persistent problem for this patient population. While opioids have their inherent drawbacks due mainly to the potential for addiction, pancreatic enzyme supplementation, central nerve blocks and antioxidants have demonstrated limited efficacy. If a new modality were available, it would be of great clinical importance in treating patient symptoms.

Many previous animal studies have been presented on the effect of intravenous secretin on acute pancreatitis. These studies have had heterogeneous results in terms of biochemical and histologic outcomes. Though no studies have shown a worse outcome with any group receiving intravenous secretin therapy, the level of improved outcome varied between modest to moderate improvement, especially with toxin induced acute pancreatitis (Lankisch, Digestion (1983) 26:187; Renner, J. Clin. Invest. (1983) 72:1081-92; Keim et al., Hepatogastroenterology (April, 1985) 32(2):91-96).

During the early 1980s, scientists began to note that intraductal pancreatic pressures in chronic pancreatitis may be elevated along with increased pancreatic secretion viscosity (Tympner, Acta Hepatogastroenterol. (1978) 25:73-76; Guy, Gastroenterology 84:102-107 (1983); Madsen, Scand. J. Gastroenterol. (1982)17:553). Based on these observations, investigators tried a variety of methods to either relieve the obstruction or decrease the viscosity within the pancreatic duct system, therefore leading to less back pressure and flares of chronic pancreatitis. Bromhexine is one of the therapeutic attempts to decrease the viscosity of pancreatic fluid. This modality was noted to be helpful in treating pancreatitis due to a mucin producing pancreatic tumors as well as in chronic pancreatitis with chronic protein plugs. Bromhexine was given alone, with radiation, or with intravenous secretin to help remove the stagnant or sludge-like pancreatic juices that were thought to be leading to recurrent pancreatitis and improved pain (Shinohara, Tando (1993) 7:527-534; Noda, Pancreas (1997) 15:209-211). Intravenous secretin was again recently tried to "flush out" the less viscous pancreatic juice, which again was a promising study to try to relieve the back pressure/sludge of chronic pancreatitis (Tsujimoto, Alcohol. Clin. Exp. Res (29)12:272S-276S).

The only human study using subcutaneous secretin as a sole therapeutic modality for chronic pancreatitis was performed in Germany by Tympner and Rosch in 1986 (Hepato-Gastroenterol. 33:159-162 (1986)). In this placebo-controlled study, twice daily injection of 800 CU (160 mcg) depot secretin was given for seven days to 20 patients. This was done under the same premise: patients with CP were noted to have elevated levels of lactoferrin, trypsin, and protein concentrations, and that if one were able to "wash out" the sticky, protein-rich secretion, improved pain may occur. Secretin therapy alone worked: it decreased the viscosity, lactoferrin and trypsin in the drug administration arm. Interestingly, a strong trend towards decreased serum amylase levels was noted. Most importantly, pain levels at the end of the study were significantly improved (p<0.05) in the study arm, even with such small numbers of participants. Unfortunately, there has never been a follow-up study from this group in which intravenous secretin therapy was studied as a sole pain modulating treatment.

Secretin has also been safely demonstrated at a dose of 6 U/kg (1.2 mcg/kg) for intravenous administration (Yamamoto, Digestive Dis. And Sci. 50:2034-2036 (November 2005)). 0.78 mcg/kg was safely given to 12 patients suffering from Zollinger-Ellison Syndrome (ZES), and these findings were confirmed in a validation cohort study (Kuiper, Pancreatology 10(1):14-18 (2010); EPub 19 Mar. 2010).

The largest parental dose of secretin administered in a study was 160 mcg twice a day per patient for 7 days. This dosing regimen was found safe and is at least 333% more than the highest dosing in this study. The 333% dose was administered for 7 consecutive days without consequences.

Various treatments for abdominal pain due to pancreatitis have been disclosed in the prior art.

For example, U.S. Pat. No. 7,459,155 discloses methods for treating abdominal pain due to pancreatitis by administering the proteolytic enzyme seaprose derived from *Aspergillus*.

U.S. Patent Application Publication US2005/0070472 discloses methods for treating pancreatitis and pain associated with it by administering amylin, amylin agonists, or amylin analogues.

U.S. Patent Application Publications U.S. 2007/0219222 and U.S. 2009/0143377 disclose methods of treating pain associated with pancreatitis by administration of transient receptor potential A1 (TRPA1) inhibitors.

U.S. Patent Application Publication U.S. 2008/0146611 discloses methods of treating pain associated with pancreatitis by administering transient receptor potential V3 channel inhibitors.

U.S. Patent Application Publication U.S. 2009/0081184 discloses methods of treating abdominal pain associated with various forms of pancreatitis by administering to the patient one or more non-pancreatic protease enzymes.

U.S. Patent Application Publication U.S. 2009/0192558 discloses methods of treating pain resulting from pancreatitis by using a device such as a microstimulator that electrically stimulates the pancreas.

U.S. Patent Application Publication U.S. 2010/0204313 discloses methods of treating abdominal pain associated with various forms of pancreatitis by administering resiniferatoxin to the patient.

What is needed in the art are compositions and methods for treating pain resulting from chronic pancreatitis that is effective yet does not suffer the disadvantages of for example narcotic addition or limited efficacy. The present invention is believed to be an answer to that need.

SUMMARY OF THE INVENTION

In one aspect, the present invention is directed to a method for treating pain resulting from chronic pancreatitis in a human patient, comprising the step of administering to a human patient suffering from pain resulting from chronic pancreatitis a therapeutically effective amount of a pharmaceutical composition comprising secretin and a pharmaceutically acceptable carrier, said pharmaceutical composition effective to treat said pain in said human patient.

This and other aspects will become apparent upon reading the following detailed description of the invention.

BRIEF DESCRIPTION OF THE FIGURES

The invention will be more fully understood from the following written description and accompanying figures in which.

DETAILED DESCRIPTION OF THE INVENTION

Figure 1:
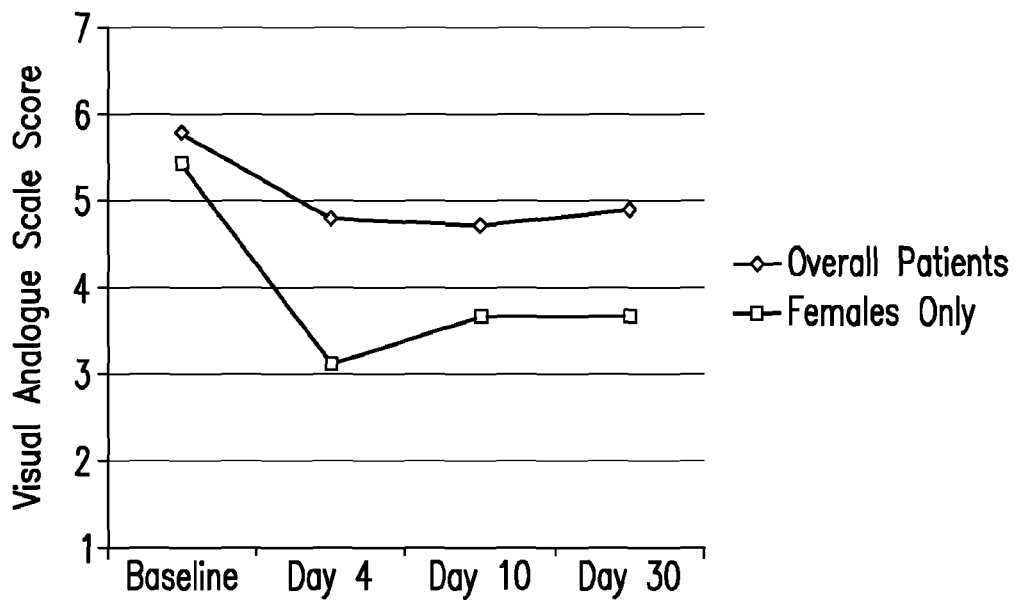
FIG. 1 is a graph showing primary outcome results for visual analogue scale measurement.

It has now been unexpectedly found that secretin is effective for treating pain associated with chronic pancreatitis (CP).

In accordance with one embodiment of the method of the present invention, treatment for pain associated with chronic pancreatitis includes administering to a patient in need of such treatment a pharmaceutical composition comprising secretin. Patients subjected to the method of the present invention can benefit from the administration of intravenous secretin to help control pain from CP. For patients on opioid analgesics, a benefit of intravenous secretin according to the method of the invention is to decrease their reliance on these medications and offer an improvement in their pain-free quality of life. Additional benefits could also include decreased nausea, decreased vomiting, decreased use of analgesics, more rapid time to resumption of oral intake, decreased length of hospitalization, decreased time to resumption of normal daily activities, and decreased time to return to work.

As indicated above, the present invention is directed to administering a therapeutically effective amount of a pharmaceutical composition comprising secretin and a pharmaceutically acceptable carrier to a patient suffering from pain associated with chronic pancreatitis. Each of these components is discussed in more detail below.

Secretin is a 3055.5 MW (27 amino acid) gastrointestinal peptide hormone originally extracted from the porcine duodenum. The primary action of secretin is to increase the volume and bicarbonate content of pancreatic juice (Gutierrez L V, et al., Gut 13:721-25 (1972); Laugier R, et al., Digestion 54:54-60 (1993); Cavallini G, et al., Dig. Dis. Sci. 37(1):93-96 (1992)). also increases the pancreatic duct diameter (Glaser J, et al., Int. J. Pancreatol. 15:195-200 (1994); Tulassay Z, et al., Gastroenterol. J. 51:47-50 (1991)) and causes sphincter of Oddi relaxation (Geenen J E et al., Gastroenterology 78:317-24 (1980); Laugier R. Endoscopy 26:222-27 (1994)). In the methods of the invention, secretin may be used from any source. Preferably the secretin used in the methods of the present invention is the naturally occurring form, the synthetic form, or the genetically recombined form of porcine, bovine or human secretin. One useful form of naturally occurring human secretin is manufactured by ChiRhoClin, Inc. (Burtonsville, Md.) with the tradename "CHIRHOSTIM". One useful form of porcine secretin is manufactured by ChiRhoClin, Inc. (Burtonsville, Md.) and sold under the trade name "SECREFLO" by Repligen Corporation (Waltham, Mass.). Another useful form of porcine secretin is manufactured by ChiRhoClin, Inc. (Burtonsville, Md.) with the tradename "SECREMAX". A useful form of human secretin is manufactured and sold by ChiRhoClin, Inc. under the tradename "SECRETIN-HUMAN".

The secretin may be combined with a pharmaceutically acceptable carrier to form a pharmaceutical composition. Thus, the pharmaceutical compositions of this invention comprise secretin from any source (including pharmaceutically acceptable salts thereof) in combination with any pharmaceutically acceptable carrier, adjuvant or vehicle. Pharmaceutically acceptable carriers, adjuvants and vehicles that may be used in the pharmaceutical compositions of the present invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride (saline), zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered by any route that produces acceptable bioavailability. Suitable administration methods include, but are not limited to, parenteral methods such as intravenous, subcutaneous and intramuscular and per os (by mouth), or sublingual, and transdermal bolus or continuous infusions of secretin may be used. Particularly useful methods of administration in accordance with the method of the invention include oral and intravenous methods. The risks associated with the use of intravenous secretin administration are minor. There has not been any serious reported adverse drug reaction to human secretin stimulation. Rarely, in the thousands of patients who have undergone pancreatic function testing with human secretin, there is flushing of the face with stable vital signs. Therefore, the risk of administrating secretin is minimal. Secretin is also not known to increase the risk of acute pancreatitis episodes in patients with CP and acute recurrent pancreatitis (ARP) not presently having an acute pancreatitis attack. No allergic reactions have been reported with secretin in commercial use although the administration of a test dose 0.2 mcg (0.1 mL) IV is still recommended. No significant hemodynamic effects have been observed following administration of secretin. Otherwise the risks of administering secretin are minimal.

The pharmaceutical compositions of the invention are preferably administered internally, e.g., intravenously, in the form of conventional pharmaceutical preparations, for example in conventional enteral or parenteral pharmaceutically acceptable excipients containing organic and/or inorganic inert carriers, such as water, gelatin, lactose, starch, magnesium stearate, talc, plant oils, gums, alcohol, VASELINE (petroleum jelly), or the like. The pharmaceutical preparations can be in conventional solid forms, for example, tablets, dragees, suppositories, capsules, or the like, or conventional liquid forms, such as suspensions, emulsions, or the like. If desired, they can be sterilized and/or contain conventional pharmaceutical adjuvants, such as preservatives, stabilizing agents, wetting agents, emulsifying agents, buffers, or salts used for the adjustment of osmotic pressure. The pharmaceutical preparations may also contain other therapeutically active materials.

The pharmaceutical preparation of the invention should include an amount of secretin effective for preventing pain from chronic pancreatitis. The effective dosage will depend on several factors, including body weight, body mass index, formulation factor, route of administration, age, gender, disease severity, and the like. Suitable dosages may be, for example, in the range of about 2 to 80 micrograms secretin, more preferably of about 8 to about 36 micrograms secretin, and most preferably between 15 and 20 micrograms secretin per dose administered via intravenous bolus. In terms of body weight, suitable dosages of the pharmaceutical composition should include 0.05 µg secretin per kg body weight to about 0.8 µg secretin per kg body weight. One particularly effective dose is 0.4 µg per kg body weight. As will be appreciated by those skilled in the art, multiple doses of secretin may be required to be administered each day over a period of time (for example, a dose of 16 micrograms secretin (approximately 0.2 micrograms per kilogram body weight) intravenously, four times per day for 7 days.

In order to achieve the above dosage ranges, it will be appreciated by those of skill in the art that the amount of secretin used with a particular form of administration will depend on absolute bioavailability of the secretin dosage and the route of administration. For example, a transdermal patch requires approximately 1 mg of secretin to achieve dosages in the above ranges. A nasal spray requires approximately 2 mg secretin per spray in order to achieve the above dosage ranges. A sublingual tablet or film requires approximately 50 mg secretin to achieve the above dosage ranges, and a tablet or capsule requires approximately 100-250 mg secretin per tablet or capsule to achieve the above dosage ranges.

EXAMPLE

The invention is further described by the following Example, but is not intended to be limited by the Examples. All parts and percentages are by weight and all temperatures are in degrees Celsius unless explicitly stated otherwise.

Background and Aims

Type B pain associated with chronic pancreatitis (CP) is often refractory to standard pain treatments. The following Example shows that intravenous secretin infusions can lead to improvements in daily pain, quality of life, and/or opiate use in patients with type B pain from chronic pancreatitis.

Materials and Methods

Patients

All included patients had been diagnosed with chronic pancreatitis (CP) based on standard cross-sectional imaging, endoscopic ultrasound and/or direct pancreatic function testing. Patients were between 18-70 years of age and had not experienced signs or symptoms of acute pancreatitis within 60 days of enrolling in the study. All patients had type B pain from CP as per the definition by Ammann (severe, unremitting pain) and all but one were taking opioids at the time of presentation (Ammann R W et al., Gastroenterology 111: 224-231 (1996)). All patients provided written, informed consent. ChiRhoStim® (human secretin for injection) was provided by ChiRhoClin Inc. Burtonsville, Md.

Study Design

The study was designed as a single-center, prospective, phase II dose-escalation trial. After initial screening, patients completed a 10 point visual analogue scale assessment of their pain at five time points during one full day prior to human secretin administration (baseline). The SF-36 score was also recorded at baseline. Finally, baseline daily opioid use was calculated and converted to morphine equivalents in milligrams.

Patients were given three intravenous bolus doses of human secretin two hours apart on each day for the first three days of the study. The infusion doses of synthetic human secretin (sHS) per the schedule in Table 1 were based on doses that have been previously reported as safe when used for other purposes (Krishnaswami S, et al., Pediatrics 2011; 127(5):e1322-5.)

TABLE 1

Study Dosing Schedule and Outcome Assessment Protocol

| Intervention | Scheme Time | sHS Dose | Visual Analog | SF-36 |
|---|---|---|---|---|
| Day 1 Dosing Schedule | | | | |
| 0 min | 0840 | | X | X |
| Test dose (0.2 mcg) | 0859 | | | |
| Dose 1 (0.5 mcg/kg) | 0900 | X | | |
| 100 min post Dose 1 | 1040 | | X | |
| Dose 2 (0.1 mcg/kg) | 1100 | X | | |
| 100 min post Dose 2 | 1240 | | X | |
| Dose 3 (0.2 mcg/kg) | 1300 | X | | |
| 100 min post Dose 3 | 1440 | | X | |
| 380 min post Dose 3 | 2100 | | X | |
| Day 2 Dosing Schedule | | | | |
| 0 min | 0840 | | X | |
| Dose 1 (0.1 mcg/kg) | 0900 | X | | |
| 100 min post Dose 1 | 1040 | | X | |
| Dose 2 (0.2 mcg/kg) | 1100 | X | | |
| 100 min post Dose 2 | 1240 | | X | |
| Dose 3 (0.4 mcg/kg) | 1300 | X | | |
| 100 min post Dose 3 | 1440 | | X | |
| 380 min post Dose 3 | 2100 | | X | |

TABLE 1-continued

Study Dosing Schedule and Outcome Assessment Protocol

| Intervention | Scheme Time | sHS Dose | Visual Analog | SF-36 |
|---|---|---|---|---|
| Day 3 Dosing Schedule | | | | |
| 0 min | 0840 | | | X |
| Dose 1 (0.2 mcg/kg) | 0900 | X | | |
| 100 min post Dose 1 | 1040 | | X | |
| Dose 2 (0.4 mcg/kg) | 1100 | X | | |
| 100 min post Dose 2 | 1240 | | X | |
| Dose 3 (0.8 mcg/kg) | 1300 | X | | |
| 100 min post Dose 3 | 1440 | | X | |
| 380 min post Dose 3 | 2100 | | | X |

Patients were blinded to the dose of sHS given, but were told that each administration was a different dose of the medication. After each administration, patients were monitored carefully for any adverse reactions. The primary investigators were blinded to all outcome assessments until the all patients had completed the study.

Outcome Measurements

The primary outcome measurements were the change in baseline VAS score, SF-36 score and opioid use at 30 days post-infusion. Secondary outcomes included any adverse events and the dose at which sHS appeared to be most efficacious.

Adverse Events

Adverse events were reported on an individualized case report form which recorded the adverse reaction, its severity, the likelihood of relationship to the study drug, the action taken and the outcome of the event. Adverse events were recorded from the time of the first sHS administration until 30 days post-administration.

Data Safety Monitoring

The primary investigator was informed of all adverse events as they occurred and completed the adverse events case report forms. An independent reviewer analyzed all of the adverse events and completed the Data Safety Monitoring Report at the conclusion of the study.

Statistics

As this study represents a pilot dose escalation study, the large number of patients normally required to power a standard trial were not utilized. The study was designed with sufficient power to determine a beneficial effect of the study group, for example, a percent improvement following drug administration. Descriptive statistics were used to describe the patient population. Continuous variables were evaluated using the two-tailed students' t-test and dichotomous variables using chi-squared analysis. All statistical evaluation was performed using Microsoft Excel (Redmond, Wash.) and Graphpad (La Jolla, Calif.) software.

Results

Patients

Twelve (12) patients (6 men) were screened and all included in the study after obtaining written, informed consent. The mean age was 42 and average length of pain from CP was 9.5 years (Table 2). All 12 patients received 9 doses of sHS, and 11 patients completed the study (1 withdrew prior to study completion). One patient had Type B pain but was at baseline intolerant of opiods and thus morphine equivalents were not established for this individual.

TABLE 2

Baseline Patient Characteristics

| Patient | Age | Years of CP | Gender | Cause | Pain (VAS) | Medications | Oral Morphine Equivalents (mg) | SF-36 |
|---|---|---|---|---|---|---|---|---|
| 1 | 49 | 9 | Female | Alcohol | 7 | Methadone 20 mg, Oxycodone 5 mg | 82.5 | 101 |
| 2 | 50 | 8 | Male | Alcohol | 5 | Fentanyl 100 mcg/hr | 200 | 106 |
| 3 | 38 | 7 | Female | Genetic | 7 | Morphine 180 mg | 180 | 114 |
| 4 | 40 | 17 | Male | Genetic, Alcohol | 7 | | | 91 |
| 5 | 56 | 10 | Male | Alcohol | 8 | Methadone 60 mg | 225 | 97 |
| 6 | 29 | 1 | Female | Idiopathic | 3 | Dilaudid 4 mg | 16 | 104 |
| 7 | 42 | 6 | Male | Alcohol | 6 | Methadone 80 mg | 300 | 101 |
| 8 | 38 | 3 | Female | Alcohol | 4.5 | Methadone 30 mg | 113 | 104 |
| 9 | 36 | 2 | Female | Alcohol | 5 | Morphine 75 mg | 75 | 103 |
| 10 | 52 | 25 | Male | Alcohol | 6 | Fentanyl 75 mcg/hr Oxycodone 15 mg | 175 | 101 |
| 11 | 25 | 11 | Male | Idiopathic | 4 | Morphine 50 mg | 50 | 98 |
| 12 | 50 | 15 | Female | Alcohol | 7 | Morphine 80 mg | 80 | 95 |
| Summary* | 42 | 9.5 | 6♂, 6♀ | 9 alcohol 2 genetic 2 idiopathic | 5.79 | | 136 | 101.3 |

*Continuous variables represent mean values

Pain

At baseline, patients had a mean VAS of 5.79. On post-treatment days 4, 10, and 30, mean pain scores were 4.80, 4.72, and 4.90 ($p=0.25$, 0.19, and 0.27 respectively) when compared to baseline. See FIG. 1. In subgroup analysis, females tended to have improved pain compared to males with overall reduction in mean pain from 5.42 at baseline to 3.67 at day 30 ($p=0.07$). There was no appreciable difference in results when performing subgroup analysis based on age or cause of underlying pancreatitis.

Opiod Usage

Figure 2:
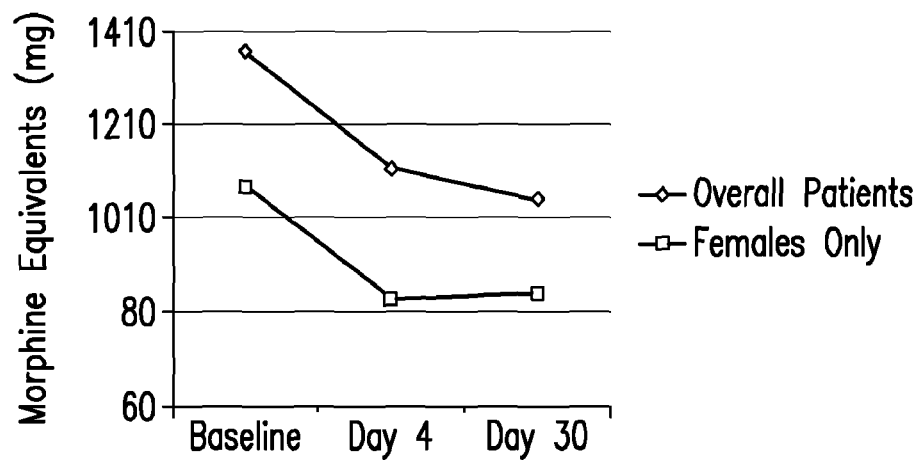
FIG. 2 is a graph showing the primary outcome results for morphine equivalent dosing.

At baseline, patients daily opioid usage (oral morphine equivalents) was 136 mg which decreased to 111 mg and 104 mg on days 4 and 30 post-therapy ($p=0.52$ and 0.34). See FIG. 2. Daily opioid equivalent in females decreased from 107 mg at baseline to 84 mg on Day 30 ($p=0.53$).

Quality of Life

Quality of life as measured by SF-36 was unaltered with therapy. Mean baseline scores were 101.3, 100.9, and 101.5 at baseline, day 4, and day 30 respectively.

Dosing Optimization

Optimal dosing appears to have been achieved, based on the change in the VAS score, after a dose of 0.4 mcg/kg. See Table 3.

TABLE 3

Human Secretin Dose-Response Curve Based on Mean VAS 100

| sHS dose (µg/kg) | Pain (VAS 0-10) |
|---|---|
| Baseline | 6.04 |
| 0.05 | 4.92 |
| 0.1 | 5.06 |
| 0.2 | 4.92 |
| 0.4 | 4.5 |
| 0.8 | 5.36 |

CONCLUSIONS

In patients, especially females, with type B pain from chronic pancreatitis requiring high doses of daily opiates, intravenous sHS administration reduced self-reported pain and opiate usage at 30 days post-infusion, although statistical significance was not achieved. These results from this study also support the possibility of central action of secretin on the brain receptors such as VIP receptors in conjunction with opioids use as well as washing the pancreatic ducts with pancreatic fluid from secretin stimulation for reduction in irritation and inflammation of the pancreas due to premature trypsin activation in the pancreatic ducts.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

What is claimed is:

1. A method for treating type B pain resulting from chronic pancreatitis in a human patient, comprising the step of administering to a human patient suffering from type B pain resulting from chronic pancreatitis a therapeutically effective amount of a pharmaceutical composition comprising secretin and a pharmaceutically acceptable carrier, wherein said pharmaceutical composition treats said pain resulting from chronic pancreatitis in said human patient; wherein the dosage of secretin administered to said patient in said pharmaceutical composition ranges from 15-20 micrograms per day, and wherein the dosage of secretin administered to said patient in said pharmaceutical composition ranges from 0.05 micrograms secretin per kg of body weight to 0.8 micrograms secretin per kg of body weight.

2. The method of claim 1, wherein the dosage of secretin administered to said patient in said pharmaceutical composition is about 0.4 micrograms secretin per kg of body weight.

3. The method of claim 1, wherein said secretin is a naturally occurring form of secretin.

4. The method of claim 1, wherein said secretin is a synthetic form of secretin.

5. The method of claim 4, wherein said synthetic form of secretin is synthetic porcine secretin.

6. The method of claim 1, wherein said secretin is a genetically recombined form of porcine, bovine, or human secretin.

7. The method of claim 1, wherein said secretin is synthetic human secretin (sHS).

8. The method of claim 1, wherein said administration step comprises intravenous administration.

9. The method of claim 1, wherein said administration step comprises oral administration.

10. The method of claim 1, wherein said pharmaceutically acceptable carrier is selected from the group consisting of ion exchangers, alumina, aluminum stearate, lecithin, serum proteins, phosphates, glycine, sorbic acid, potassium sorbate, partial glyceride mixtures of saturated vegetable fatty acids, water, salts, electrolytes, protamine sulfate, sodium chloride, zinc salts, colloidal silica, magnesium trisilicate, polyvinyl pryrrolidone, cellulose-based substances, polyethylene glycol, sodium carboxymethylcellulose, polyacrylates, waxes, polyethylene-polyoxypropylene-block polymers, polyethylene glycol and wool fat, and combinations thereof.

11. The method of claim 1, wherein said pain is abdominal pain.

12. The method of claim 1, wherein said pharmaceutical composition further comprises one or more excipients selected from the group consisting of water, gelatin, lactose, starch, magnesium stearate, talc, plant oils, gums, alcohol, petroleum jelly, and combinations thereof.

13. The method of claim 1, wherein said pharmaceutical composition further comprises one or more pharmaceutical adjuvants selected from the group consisting of preservatives, stabilizing agents, wetting agents, emulsifying agents, buffers, salts, and combinations thereof.

* * * * *